United States Patent [19]

Hansen et al.

[11] Patent Number: 5,487,201
[45] Date of Patent: Jan. 30, 1996

[54] DISPOSABLE TOOTH AND GUM CLEANING DEVICE

[76] Inventors: Bryan C. Hansen; Sharon A. Hansen, both of 198 Driftwood Trail, McHenry, Ill. 60050

[21] Appl. No.: 106,135

[22] Filed: Aug. 13, 1993

[51] Int. Cl.[6] .............................. A46B 5/04; B65D 81/20
[52] U.S. Cl. ..................... 15/104.94; 15/227; 15/104.93; 132/309; 132/323; 601/139; 206/361; 206/581
[58] Field of Search .................................. 15/167.1, 227, 15/104.93, 104.94; 132/323, 324, 309; 601/139; 206/209.1, 362.3, 209, 361, 362.1, 362.2, 206, 216, 581

[56] References Cited

U.S. PATENT DOCUMENTS

| | | | |
|---|---|---|---|
| 1,157,413 | 10/1915 | Nesper | 15/227 |
| 2,386,085 | 10/1945 | Babel | 15/167.1 |
| 3,124,824 | 3/1964 | Lutz | 15/227 |
| 3,298,507 | 1/1967 | Micciche | 15/104.94 |
| 3,368,668 | 2/1968 | Micciche | 15/167.1 |
| 3,534,887 | 10/1970 | Ginsber | 15/104.94 |
| 3,608,566 | 9/1971 | Storandt | 15/227 |
| 3,675,264 | 7/1972 | Storandt | 15/104.94 |
| 3,902,509 | 9/1975 | Tundermann et al. | 15/227 |
| 3,934,299 | 1/1976 | Regester | 15/104.94 |
| 4,105,120 | 8/1978 | Bradberry | 132/323 |
| 4,292,705 | 10/1981 | Stouffer | 15/227 |
| 4,617,694 | 10/1986 | Bori | 15/227 |
| 4,875,247 | 10/1989 | Berg | 15/227 |
| 5,107,562 | 4/1992 | Dunn | 15/227 |
| 5,184,719 | 2/1993 | Gordon | 206/209.1 |
| 5,213,428 | 9/1993 | Salman | 15/167.1 |
| 5,228,433 | 7/1993 | Rosen | 15/227 |
| 5,320,531 | 6/1994 | Delizo-Madamba | 15/227 |
| 5,348,153 | 9/1994 | Cole | 15/227 |

*Primary Examiner*—David Scherbel
*Assistant Examiner*—Gary X. Graham
*Attorney, Agent, or Firm*—Charles F. Meroni, Jr.

[57] ABSTRACT

An oral wipe comprised of a sleeve, the sleeve being comprised of interwoven material, the sleeve having a closed end extending to at least one corner at the closed end, a pick element comprised of a heat sealable component, and a piece of dental floss, the piece of floss having one floss end embedded and retainingly secured in the heat sealable component.

19 Claims, 10 Drawing Sheets

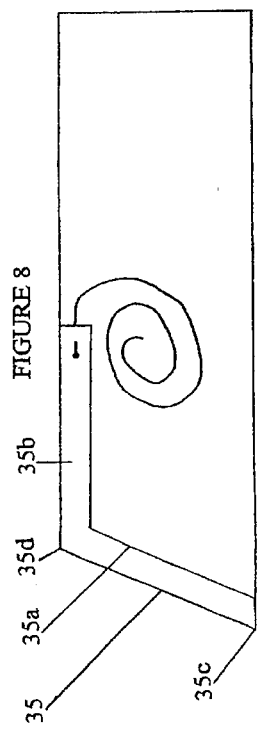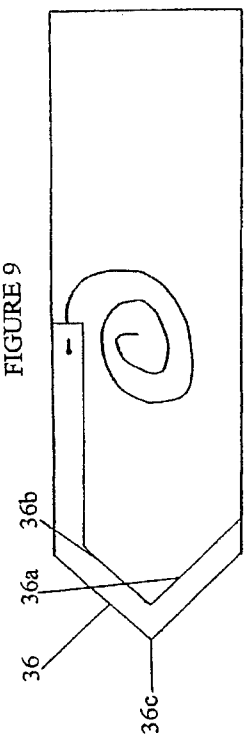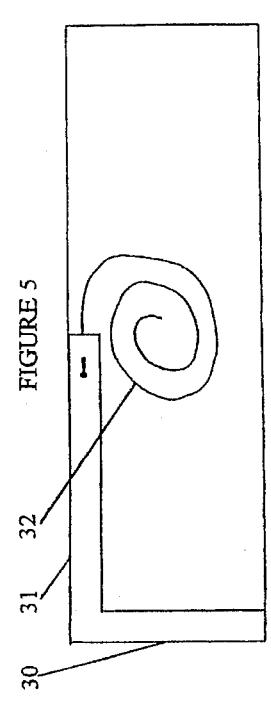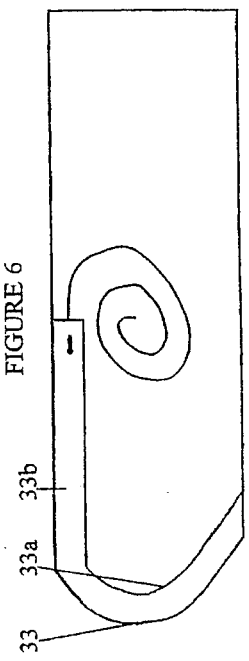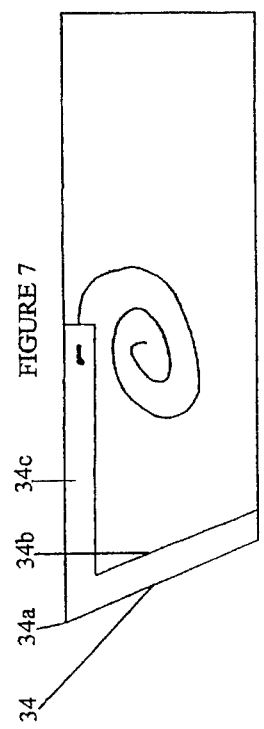

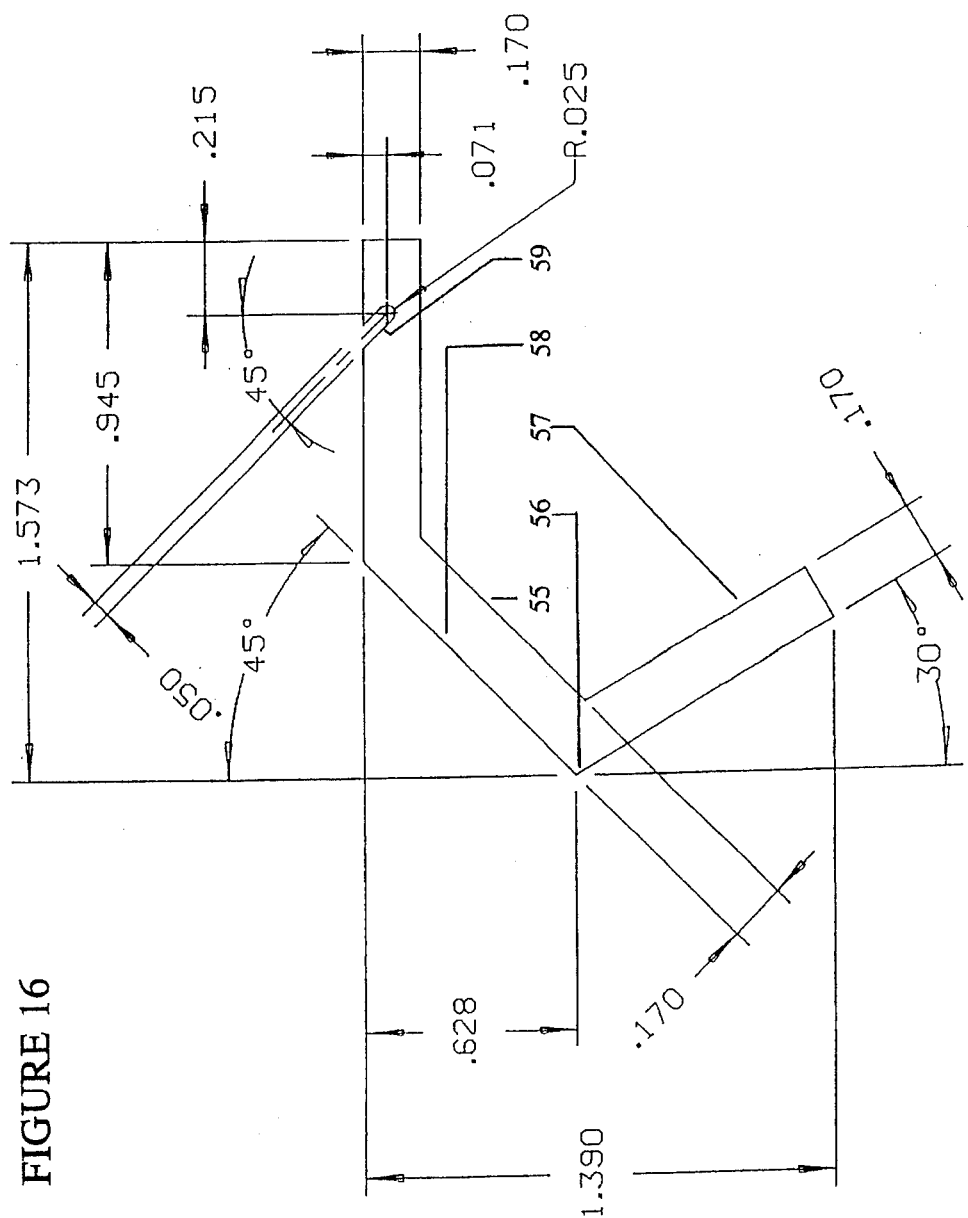
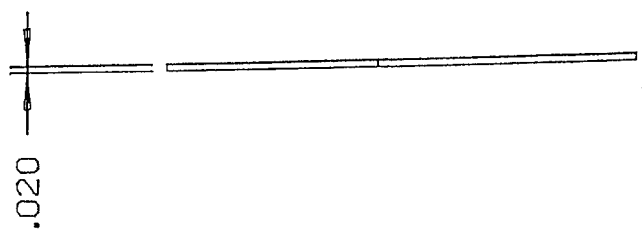
FIGURE 16

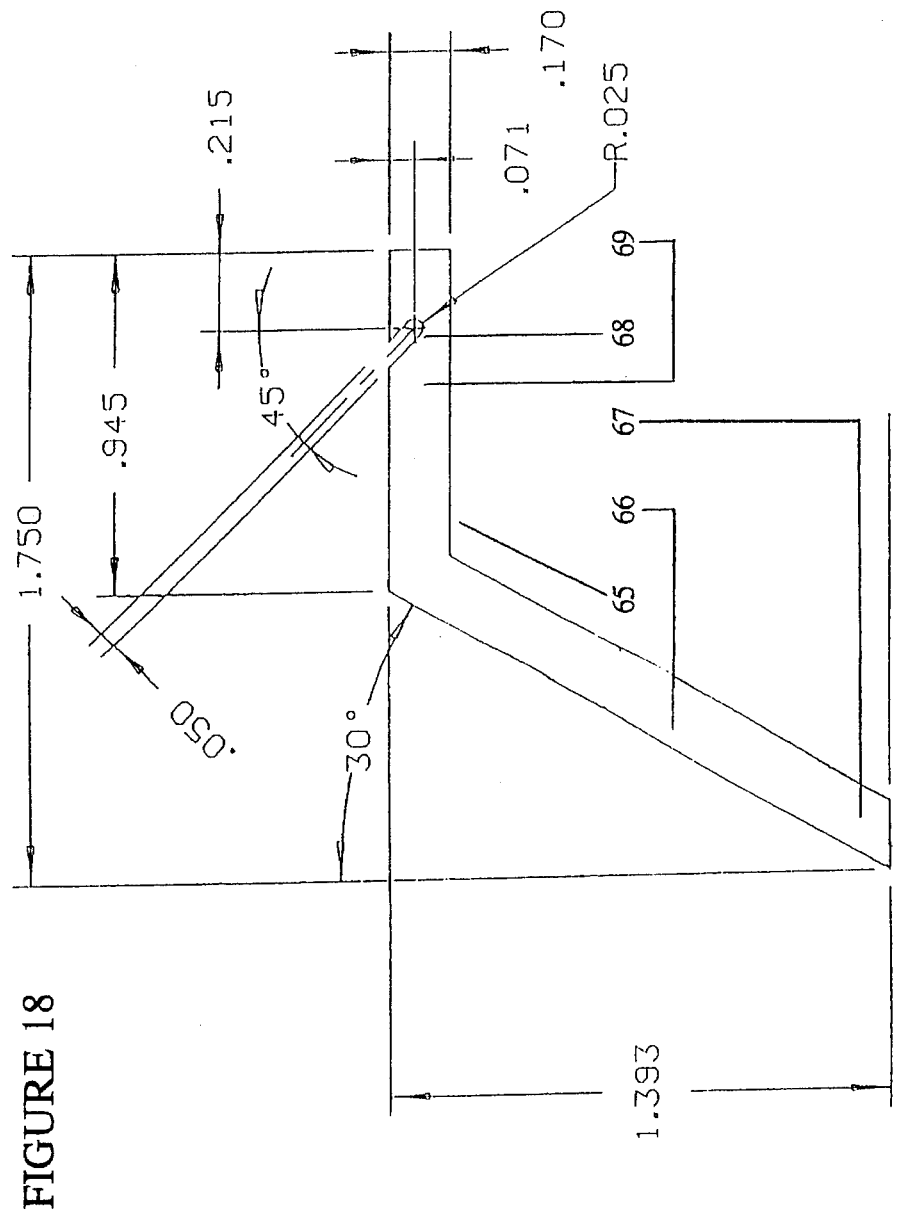
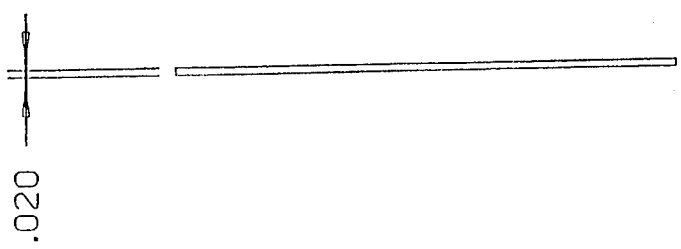
FIGURE 18

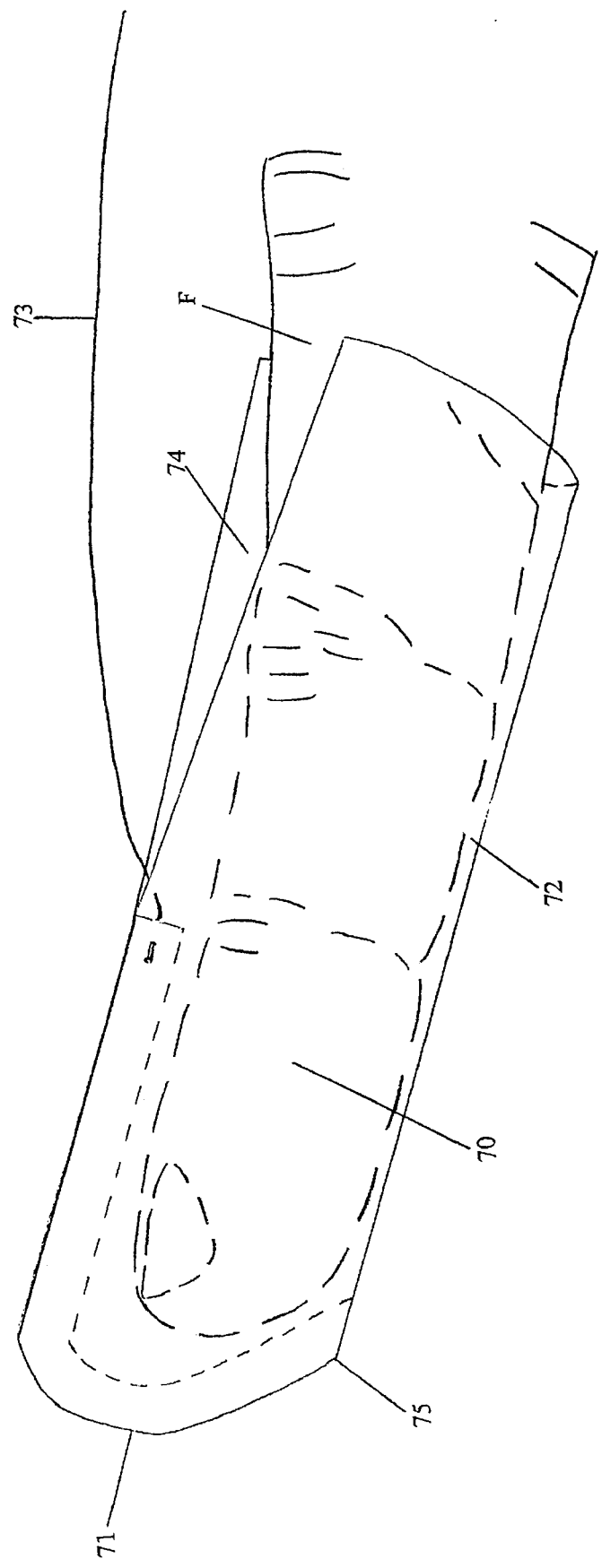

DISPOSABLE TOOTH AND GUM CLEANING DEVICE

BACKGROUND OF THE INVENTION

1. Field of Invention

Our oral wipe or oral wipe device is adapted to be utilized by mounting the device on a finger of a hand, such as a forefinger, and when so mounted it is then rubbed against the teeth and/or gums of the user to remove plaque and food particles from in between teeth and from a tooth surface and also from gum tissue. Our device or product is disposable and is most desirably used when the user cannot readily utilize a toothbrush and toothpaste for the purpose of oral hygiene. The device has a reinforced front edge which acts as a pick and is used to clean the area in between the teeth. The body of the device can be used to remove plaque and food particles from the teeth and gum surfaces. A length of dental floss is fixedly attached to the device and enables the user to floss the users teeth to further remove food particles from areas surrounding the teeth. In order that a user will be left with a pleasantly fresh taste after using our device, we have saturated the oral wipe device with a mouth wash type substance which can have a peppermint or spearmint flavor, as desired.

2. Description of the Prior Art

Various disposable tooth cleaning devices have been known before and typical prior art devices are shown in U.S. Pat. Nos. 3,675,264; 4,292,705; 4,875,247; and 5,107,562.

The U.S. Pat. No. 3,675,264 shows the use of floss as described in columns 1 and 4 of the patent. Here, the patentee does not have the floss secured inside the dentifrice applicator at the area of the heat seal.

Another patent of interest is U.S. Pat. No. 4,292,705 where the patentee has illustrated a Tongue Toothbrush where the toothbrush is comprised of a hollow, pliable body made of thin film material to envelope an outer portion of a tongue. Mounted on the pliable body is a length of dental floss indicated at 19. The tip portion 6 of the body is utilized to massage the gums of the user. Provided on the side of the body is a storage chamber 24 where a length of dental floss thread 19 is stored. This thread is then drawn out of the storage chamber and can be attached to a lug as indicated at 18 in FIG. 5.

A further patent of interest is U.S. Pat. No. 4,875,247 where the patentee describes his disposable tooth cleaning and polishing apparatus. Here, the inventors, in column 5, discuss the idea of impregnating flexible paper material with breath freshening agents and other additives for enhancing polishing and cleaning abilities.

Another recent patent is U.S. Pat. No. 5,107,562 and this patent shows a disposable finger-mounted toothbrush where the patentee employs a flexible bag with an end of the bag having bristles, the bag being shaped for receipt of a forefinger of a user.

SUMMARY OF THE INVENTION

According to certain features of our invention we have provided an oral wipe comprised of a sleeve, the sleeve being comprised of interwoven material, the sleeve having a closed end extending to at least one corner at the closed end, a pick element comprised of a heat sealable component, and a piece of dental floss, the piece of floss having one floss end embedded and retainingly secured in the heat sealable component.

According to further features of our invention we have provided an oral wipe which is composed of three components: 1) A folded sleeve comprised of a cellulose material which is interwoven with polypropylene fibers (approximate weight to weight ratio of the fibers is 80% cellulose and 20% polypropylene); 2) A low density polyethylene component which when heat sealed, the low density polyethylene thermochemically bonds one open end of the folded sleeve as well as securing a floss material, this material in turn acts as a pick device; and 3) The floss has one end placed through an aperture in a V-shaped low density polyethylene pick component prior to heat sealing and when the heat sealing process occurs, one end of the floss is firmly secured to the oral wipe device.

Yet other features of our invention concern an oral wipe having and open ended sleeve comprised of an interwoven material that is approximately 80% cellulose and 20% polypropylene, the sleeve having a closed end extending to at least one corner at a closed end, a pick element comprised of a heat sealable low density polyethylene, an opening in the pick element, and a piece of dental floss, the piece of floss having one floss end positioned within the sleeve in the opening in the pick element, and heat seal means securing the one floss end in integral assembly with the pick element.

According to method features of our invention we have provide a method of manufacturing an oral wipe device comprising the steps of folding a piece of interwoven material that is approximately 80% cellulose and 20% polypropylene providing a folded strip having an open side, providing a length of low density polyethylene for insertion into the folded strip, connecting an end of a length dental floss with the length of low density polyethylene, heat sealing the length of low density polyethylene in the open side of the folded strip with the folded strip while also heat sealing the dental floss to permanently secure the end of the dental floss to form a piece of folded interwoven material into a closed ended sleeve having an open end for receipt of a human finger with the dental floss being left in the closed ended sleeve preparatory to overwrapping the sleeve with a protective package for sanitary purposes.

Still further features of our invention we have provide a method of manufacture of our oral wipe device wherein the device is enclosed in an open ended pouch, the oral wipe device is then saturated with a mouth wash, the pouch is further heat sealed to close an open end through which the oral wipe device was inserted into the pouch.

BRIEF DESCRIPTION OF THE DRAWINGS

FIG. 5 is an enlarge vertical section of a modified form of our oral wipe;

FIG. 6 is another modified form of our oral wipe;

FIG. 7 is still another modified form of our oral wipe,

FIG. 8 is yet another modified form of our oral wipe;

FIG. 9 is a further and still other modified form of our oral wipe;

FIG. 16 is an enlarged side elevation of the stiffening device shown in FIG. 4;

FIG. 18 is an enlarged side elevation of a still another stiffening device as seen in FIG. 7; and FIG. 19 is an enlarged fragmentary side elevation shown in full and dotted lines illustration the position of a finger in our oral wipe device which device is also illustrated in FIG. 6, only here the dental floss is moved into an extended position in readiness for use.

DESCRIPTION OF THE PREFERRED EMBODIMENT

Figure 1:
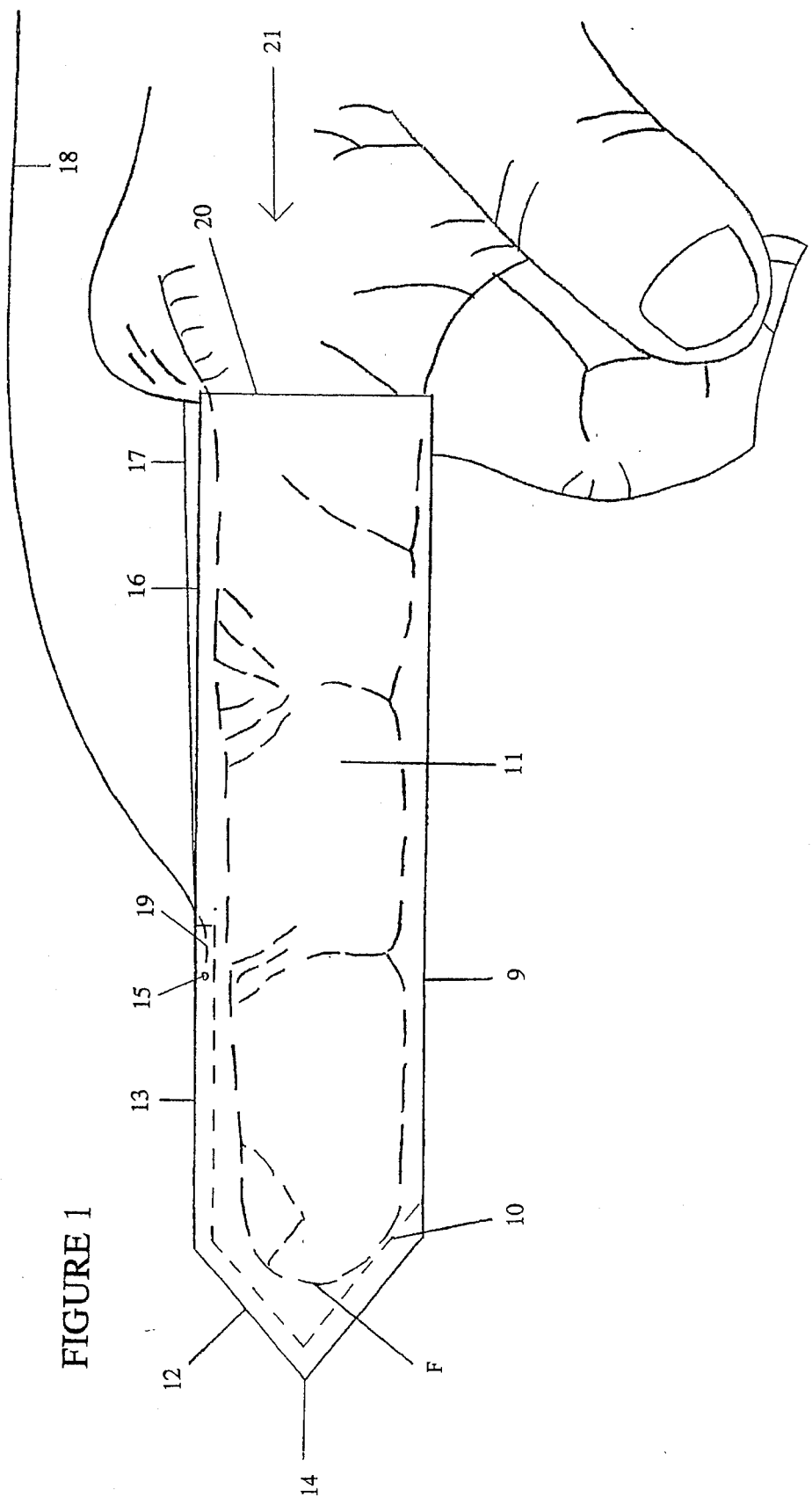
FIG. 1 is an enlarged fragmentary perspective view shown in full and dotted lines illustrating our oral wipe which can be used for the purpose of cleaning gums and teeth of a person.

The reference numeral 9 indicates our sleeve shaped oral wipe or oral wipe device which embodies our invention. Also according to our invention, we have provided a pick device or element 10 which is to be secured integrally with the oral wipe and more particularly with the folded piece of an interwoven material that is approximately 80% cellulose and 20% polypropylene 11. The pick device or element 10 is comprised of a low density polyethylene and it is preferably formed as a single ply of a one rail thickness. The element 10 is V-shaped and conforms to the shape of the folded interwoven material 11. Other shaped elements 10 can be used as hereafter discussed. Also other types of heat sealable synthetic plastics or heat sealable materials might also be substituted for the low density polyethylene here being suggested for uses in our preferred embodiment.

The heat sealable polyethylene material constitutes the ingredient or component which enables the other parts including the floss and the composite material comprised of the 80% organic and 20% polypropylene all to be thermochemically bonded and formed together as a single entity. The inclusion of the polypropylene is primarily to add tensile strength to the oral wipe 9.

This piece 11 has a closed heat sealed end 12 and a partially closed heat sealed side 13 located at edges of the sleeve. In addition, the folded piece of interwoven material 11 has a thickened sleeve corner or tooth and gum cleansing tip 14 provided generally at the closed end of the V shaped element.

The thickened sleeve corner 14 provides a sturdy point where the thickened sleeve corner 14 can be used as a pick to clean areas between teeth and the like in a situation where a human finger F is moved into the sleeve and then the assemblage is moved into the mouth for oral cleansing.

The sleeve shaped oral wipe 9 also has a pair of upper disconnected edges as indicated at 16 and 17 so that a finger can be more easily inserted into the sleeve and against the thickened sleeve corner 14.

In order to further facilitate cleansing of a person's teeth, we have provided a piece of floss 18 having a floss end which is secured in a hole 15 or the V-shaped pick device 10 to anchor the embedded floss end 19 so that it can not be easily pulled out of where it is embedded in heat sealed assembly with the material forming the thickened sleeve corner 14. The floss can be of any suitable type or thickness that is normally sold in the marketplace for consumer use by the public at large. When the floss 18 is in a storage position, it can be coiled and stored inside of the V-shaped piece 11. When it is desired to use the floss 18, the floss can be uncoiled and then moved so that it extends outwardly of an open end 20 of the sleeve shaped oral wipe 9.

We have also provided an arrow 21 which shows the direction of entry of the finger F when it is caused to be moved into the open end 20 of the sleeve shaped oral wipe preparatory to use for cleansing of the oral cavity.

Figure 3:
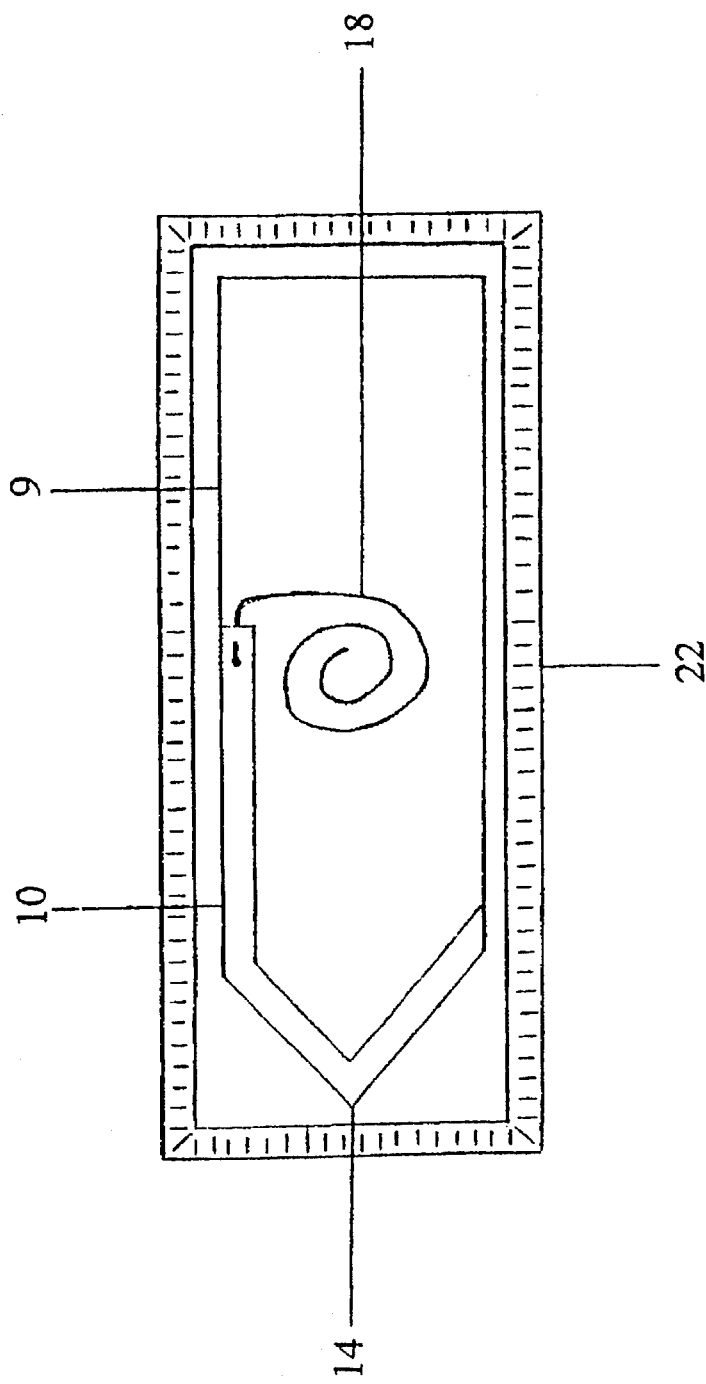
FIG. 3 is a vertical section through the oral wipe showing dental floss coiled internally thereof in readiness for use.
Figure 4:
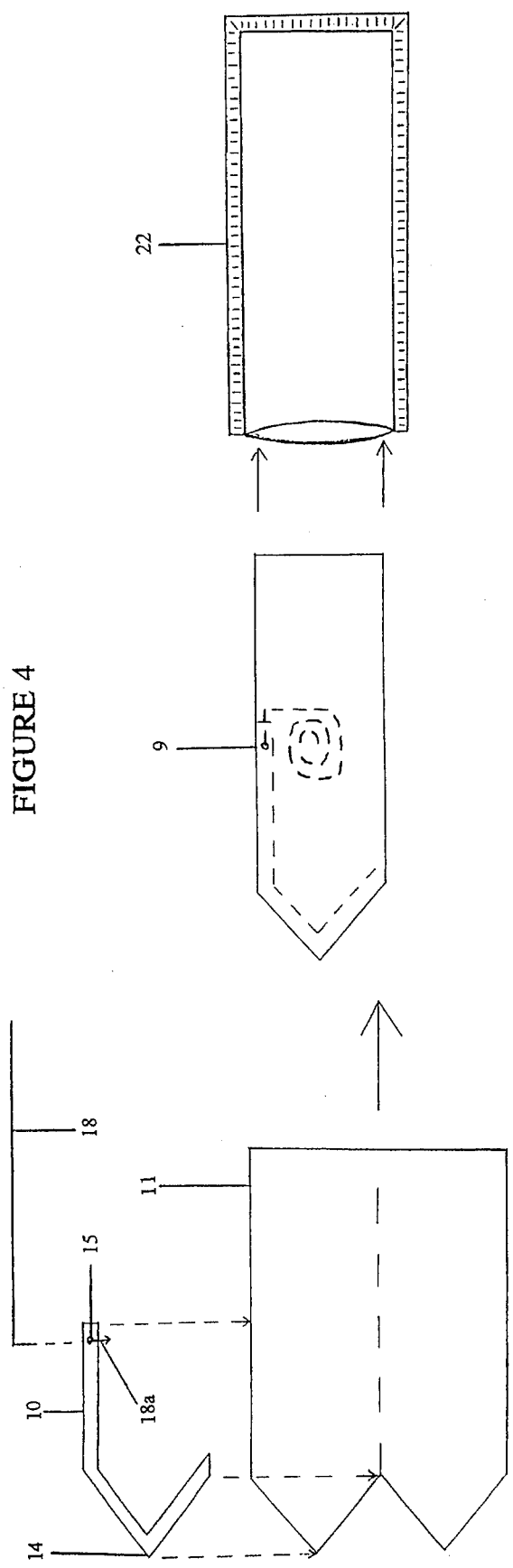
FIG. 4 is an exploded view showing the components of our wipe.

As seen in FIGS. 3 and 4, we have provided a pouch 22 for receipt of the oral wipe 9. It is intended that this pouch be provided to maintain the oral wipe device 9 in a sanitary condition in readiness for use by the ultimate user. Any suitable material can be used for the manufacture of the pouch 22. We have found that excellent results can be attained where the entire oral wipe is inserted into the pouch prior to sterilization and in this case the pouch can be manufactured from a heat sealable aluminum type material or is known as an overpouch. Overpouches of this type are well known in the art.

We have also found that where we have used an interwoven material that is 80% cellulose and 20% polypropylene, that excellent results can be attained by saturating the material with a mouthwash so that when the sleeve shaped oral wipe is placed into a person's mouth it will create a cleansing refreshing feeling inside the mouth of the user.

The device 9 would be saturated with a mouthwash or a mouthwash substance at the point it has been placed in an overpouch with three open ends sealed, and the pouch would be sealed on three ends. The device 9 would be placed inside the pouch and then the device would be saturated with the mouthwash and the open end would be sealed.

Excellent results can be attained where the V-shaped folded piece of interwoven material 11 has a vertical height of about 1.5 inches and a length of approximately 3 inches. The dental floss can be of varying lengths but excellent results are attainable where the floss has a length of approximately 6 inches. We have also found that excellent results can be attained where the V-shaped folded piece of interwoven material comprised of 80% cellulose and 20% polypropylene is single-ply.

The top sealed edges as indicated at 13 can be comprised of a polymer which thermal chemically bonds to the towel surface. By constructing the sleeve 9 as described, there will be no need for applying an adhesive for closing the sleeve at its open side at 13.

In FIGS. 5-9, inclusive, we have illustrated a series of different types of picks or pick devices. In FIG. 5 the pick device is indicated generally at 30 and is of a right angular configuration. In this instance, the sleeve shaped oral wipe 31 has a piece of dental floss 32 that is anchored to the pick device 30 in the same way as previously described. It will further be noted that the floss shown in FIGS. 6, 7, 8 and 9 also are anchored to different types of pick devices indicated at 33 in FIG. 6, 34 in FIG. 7, 35 in FIG. 8 and 36 in FIG. 9. The pick in FIG. 6 identified at 33 has a rounded end identified at 33a with a rearwardly extended arm 33b and the floss is anchored to the arm 33b in the same way as noted before. In FIG. 7 the pick 34 has a pointed end 34a, an inclined pick end 34b and an extended pick arm 34c with the parts 34b and 34c merging together to provide the pick end 34a.

In FIG. 8, the pick 35 includes a forwardly inclined leg 35a which is joined to an extended arm 35b to which the floss is attached as previously described. This pick 35 has two pick edges or pick points 35c and 35d and either of these points can be used for cleaning crevices between a person's teeth.

Now turning to FIG. 9, we still see another type of pick 36. In this instance, the pick 36 has a pair of pick ends 36a and 36b which are approximately of the same length and which converge at a point indicated at 36c that is provided for cleaning between a person's teeth as previously discussed. In all of the Figures just described including FIGS. 5–9, inclusive, it will be seen that the picks are all secured in heat sealed assembly with an oral wipe that is comprised of a V-shaped folded piece of combination cellulose and polypropylene interwoven material.

Figure 10:
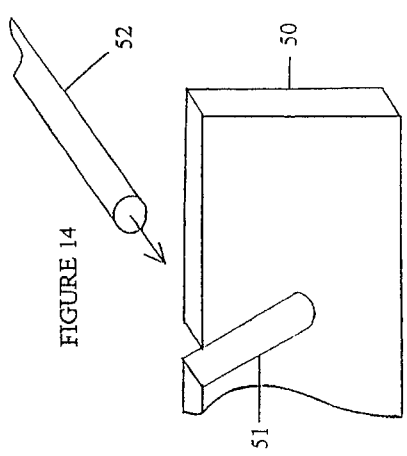
FIG. 10 is an enlarged fragmentary perspective view showing the way in which dental floss can be assembled with a stiffening device for our oral wipe.
Figure 11:
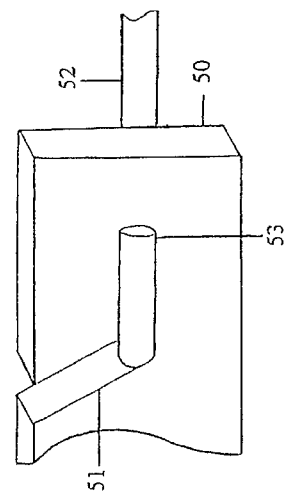
FIG. 11 shows a further step illustrating how the dental floss is secured with the stiffening device.
Figure 12:
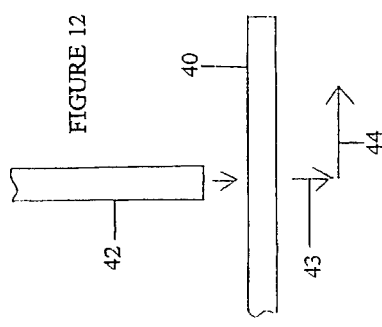
FIG. 12 is an enlarged fragmentary plan view showing yet another way in which the dental floss can be secured our oral wipe.
Figure 13:
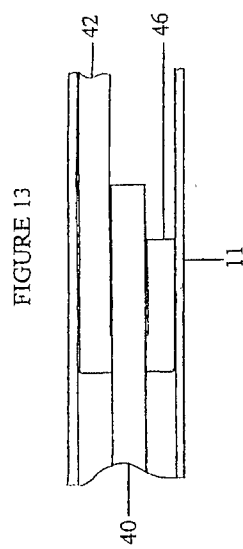
FIG. 13 shows an enlarged fragmentary plan view illustrating the way in which the floss can be secured with our oral wipe.

FIGS. 10–15 show different ways for securing floss such as indicated at 18 and 32 to the pick as noted by a number of different numbers including the pick 10. In FIGS. 10 and 11 we have identified the pick with the number 40 having a hole 41. Floss is indicated at 42 and the arrows 43 show the direction that the floss is moved through the hole 41 and then turn in the direction indicated by the arrow 44 so that floss 42 has a portion 45 extending through the hole 41 and then terminates in a reverse bent terminal floss end 46 shown in FIG. 11. FIGS. 12 and 13 illustrate the same subject as shown in FIGS. 10 and 11 only from a plan or edge perspective or vantage point.

Figure 14:
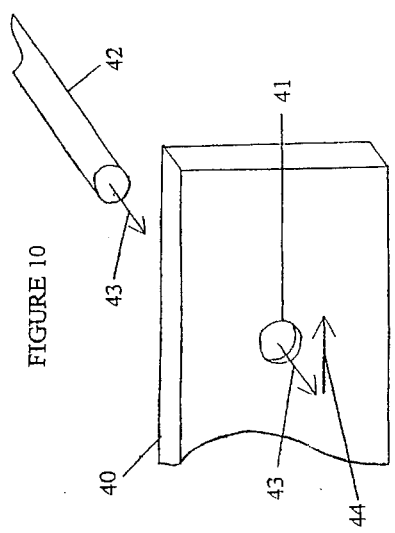
FIG. 14 illustrates yet another way in which dental floss can be secured to a modified type of stiffening device having a slot for receiving an end of the dental floss.
Figure 15:
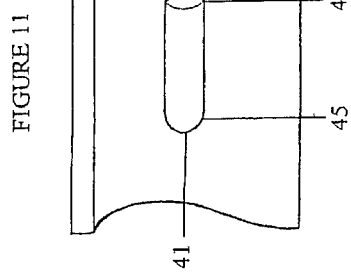
FIG. 15 is a view similar to FIG. 14 only illustrating the dental floss shown mounted in the slot with an end bent so that the floss cannot readily be pulled away from the stiffening device.

In FIGS. 14 and 15 we have shown still another embodiment where a pick device 50 is provided with an inclined slot 51. Here a piece of floss 52 is inserted into the slot 51 and floss end 53 is returned bent in the same way as previously described with the returned bent end 46. Thus it will be seen that it is contemplated that there are different ways that a piece of floss can be anchored to the pick device. In FIG. 10 we see that a hole 41 is used and in FIG. 14 we see that an angled slot 51 is used. In all cases, when the device 10 is heat sealed to secure the components together including the pick device, the piece of interwoven material and the floss, these components become bonded during the heat sealing process and it is important that the floss be securely secured to the pick device so that it cannot pull free when the user uses the floss to clean the users teeth.

Shown in FIG. 16 is another type of a pick device indicated generally at 55. This pick device has a point 56 which is where the angular point legs converge, the point legs being indicated at 57 and 58. Here, the pick device 55 is provided with an angled slot 59 for receipt of a piece of dental floss (not shown) in the manner previously illustrated and discussed in FIGS. 14 and 15. This Figure is particularly noteworthy for the purpose of assisting a man skilled in the art in the manufacture of a pick device such as indicated at 55 as the drawing shows the dimensions and the angles required for manufacture.

Figure 17:
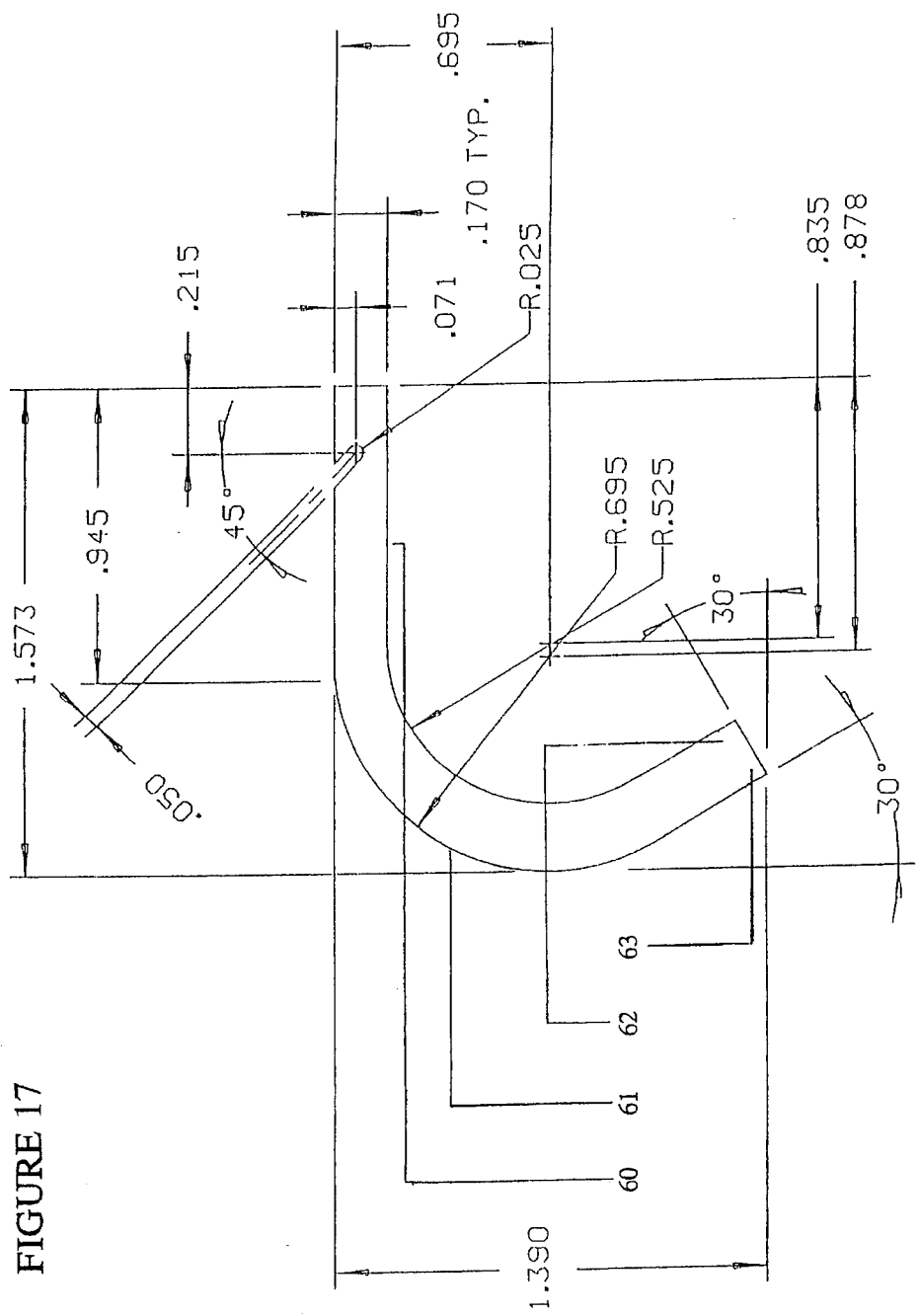
FIG. 17 is an enlarged side elevation of yet another stiffening device as illustrated in FIG. 6.

In FIG. 17 we have shown still another pick device indicated generally at 60. This pick device is also illustrated in full detail with the angles and the dimensions as previously described in connection with FIG. 16. The pick device 60 has a curved or rounded end 61 which terminates in a return bent pick terminal 62 having a point 63 for use in cleansing of a person's teeth so that the pick end 63 can be maneuvered back and forth along and through the crevices between a person's teeth. As stated, the pick device 60 shown in FIG. 17 also has the dimensions and angles required to manufacture this device to assist a person skilled in the art in reproducing the present invention.

Shown in FIG. 18 is still another pick device indicated generally at 65. This pick device has a diagonally outwardly or forwardly extending pick leg 66 with a pointed terminal end 67 for use in cleansing the crevices located between a person's teeth. Once again the pick device 65 has the dimensions and angles required for the manufacture of this particular pick device 65. An angled floss slot 68 is provided and it will be noted that this slot extends in a direction that will converge with the leg 66 if the leg 66 were extended beyond a base pick leg 69 of the pick 65.

In FIG. 19 we have shown a sleeve shaped oral wipe 70 having a pick device or element 71 which is identical to the one shown in FIG. 17. Here our pick device has a V-shaped sleeve 72 and it will be seen that a finger F has been inserted in the sleeve 72 and a piece of floss 73 extends out through an open end 74 of the sleeve 72. When the finger is in place internally of the sleeve shaped oral wipe 70, an inner end of the finger almost contacts the pick device 71. The pick device 71 has a lead end 75 that can be used to probe into the crevices between a person's teeth for cleansing purposes.

Method of Manufacture

Figure 2:
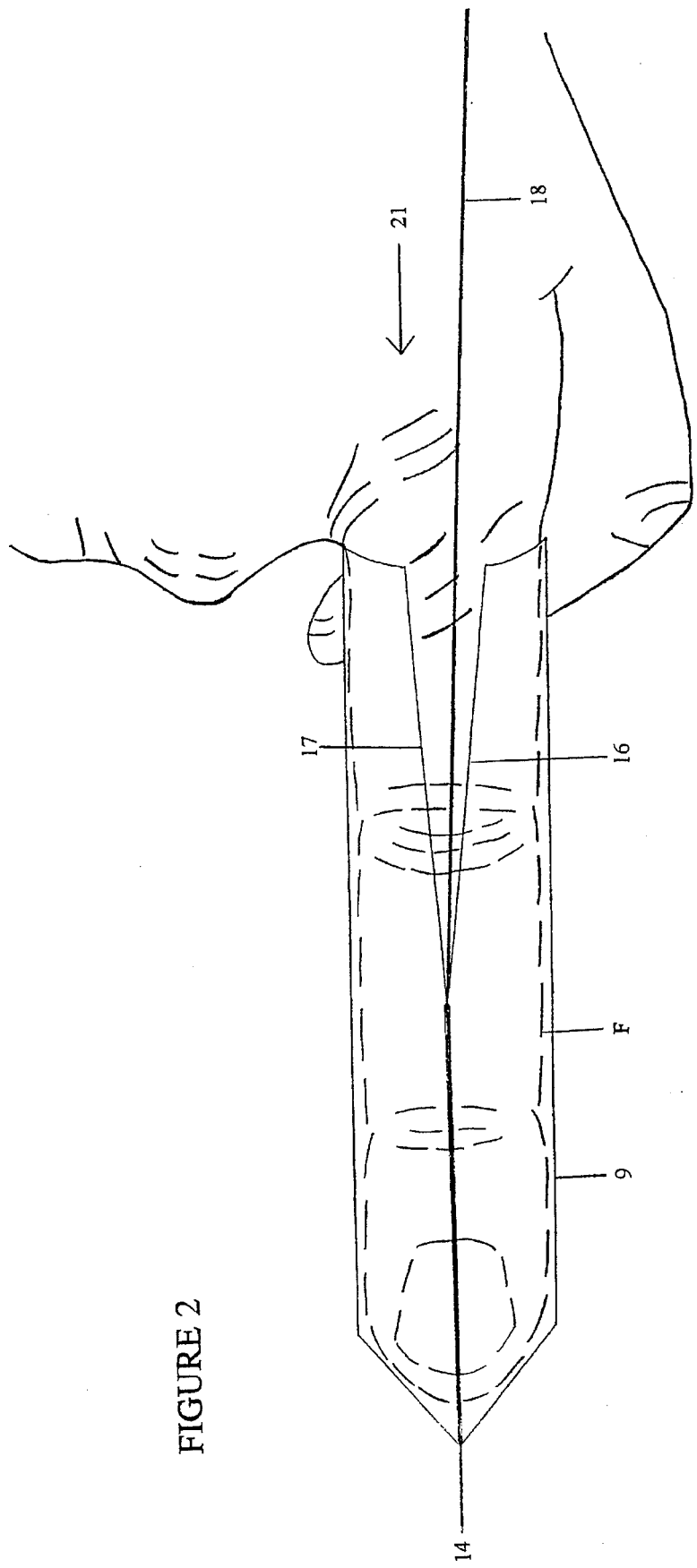
FIG. 2 is an enlarged plan view of the oral wipe illustrated in FIG. 1.

In connection with the manufacture of our oral wipe device, it will be appreciated that this device can be made by first folding a piece of interwoven material comprised of 80% cellulose and 20% polypropylene to form a folded strip having an open side. This procedure is generally shown in FIG. 4 at 11. Thereafter, the V-shaped pick device 10 comprised of heat sealable low density polyethylene is cut out to be provided with an angled end or point as indicated at 14 while at the same time cutting the hole 15 for receipt of the floss 18. At this point in time, after the device 10 has been formed to shape, the floss is inserted through the hole 15 in the direction indicated by the arrow 18a as seen in FIG. 4. This sub-assembly is then put inside of the V-shaped folded piece of interwoven material 11 and the components are then subjected to a heat sealable operation to secure them into summary together as generally seen in FIGS. 1 and 2 such that a heat seal is formed extending partially along longitudinal edges of an open side of the folded piece coupling the edges of the sleeve to thereby provide a open ended sleeve. Upon the formation of this sleeve shaped oral wipe 9, it can then be inserted into the pouch or bag indicated generally at 22 in FIGS. 3 and 4. This pouch or bag normally would be provided with 3 heat seals on three sides and an open end for receipt of the oral wipe. Once the oral wipe device 9 has been inserted into the pouch 22, then the interior of the pouch can be sprayed with a mouthwash substance to saturate the material of the sleeve 11 and particularly the cellulose fibers so that when the device 9 is removed from the pouch 22, it will still be damp and then be able to convey a mouthwash flavor to the person's mouth when the oral wipe is used for cleansing the gums and teeth of a person. Recapitulating, after the oral wipe device 9 has been inserted into the pouch 22, the open end is then sealed to completely close the device. At this point, the pouched device will be subjected to an Impirical sterilization process to ensure product sterility. This device could alternately be produced under aseptic conditions.

In the manufacture of our oral wipe device 9 it will be understood that these types of devices can be produced in a production machine.

To manufacture a large quantity of oral wipe devices, a continuous single roll of the interwoven cellulose/polypropylene material would be folded, the V-shaped heat sealable low density polyethylene component with the floss already in place would inserted into the folded interwoven material. At this point the components would be pressed together and heat sealed. After heat sealing, a delay of a few seconds will allow the v-shaped heat sealed low density polyethylene material to solidify. A cutting die would then cut the leading and trailing sections of the device. The floss should be held upward and out of the way as to not interfere with the cutting of the leading and the tailing end of the interwoven material. The oral wipe device would then drop down into another line where it would then be packaged, saturated with mouth wash, the overpouch sealed and entire pouched unit sterilized.

With regard to the illustrated form of our invention where the floss is shown coiled inside of the pouch, we have also considered another alternative where the oral wipe 9 would be folded in half and then the floss would be wound circularly in coils around the folded oral wipe. By folding the oral wipe in half and coiling the floss around the oral wipe, then the size of the pouch used to contain the oral wipe can be made smaller to save packaging expense.

While the preferred form of the invention has been specifically illustrated and described herein, it will be apparent to those skilled in the art that modifications and improvements may be made to the form herein specifically disclosed. Accordingly, the present invention is not to be limited to the form herein specifically disclosed or in any other way inconsistent with the progress in the an promoted by this invention.

We claim:

1. An oral wipe comprising an elongated sleeve, the sleeve being formed of an interwoven material, the sleeve having a closed end defining at least one corner, the sleeve having an open end to enable a finger to be readily inserted in the sleeve, the sleeve having at least one edge therealong, a pick element formed of a heat sealable material different from said interwoven material the sleeve being heat sealed to the pick element along said at least one edge of the sleeve and at said closed end, a piece of dental floss, the piece of dental floss having one floss end embedded and retainingly secured in said heat sealable material.

2. The oral wipe of claim 1 wherein the piece of dental floss is coiled and housed in said sleeve for storage purposes.

3. The oral wipe of claim 2 wherein the piece of dental floss can be withdrawn from the sleeve and uncoiled in readiness for use.

4. The oral wipe of claim 1 wherein the sleeve is saturated with a mouth wash.

5. The oral wipe of claim 1 wherein the sleeve has a partially open side remote from said corner to enable a finger to be readily inserted in said sleeve.

6. The oral wipe of claim 1 wherein the sleeve is comprised of a folded piece of the interwoven material comprised of approximately 80% cellulose and 20% polypropylene fibers, and a heat seal extending partially along longitudinal edges of an open side of the folded piece coupling the edges of the sleeve to thereby provide a open ended sleeve.

7. The oral wipe of claim 1 wherein the sleeve is comprised of a folded piece of the interwoven material comprised of approximately 80% cellulose and 20% polypropylene fibers.

8. An oral wipe comprising an open ended elongated sleeve formed of an interwoven material that is approximately 80% cellulose and 20% polypropylene, the sleeve having a closed end having at least one corner, a pick element comprised of a heat sealable low density polyethylene attached to the sleeve, the pick element having an opening, a piece of dental floss, the piece of dental floss having one floss end positioned within said sleeve in said opening in said pick element, and heat seal means securing said one floss end in integral assembly with said pick element.

9. The oral wipe of claim 8 wherein the piece of dental floss is coiled and housed in said sleeve for storage purposes.

10. The oral wipe of claim 9 wherein the sleeve has an open sleeve end, the piece of dental floss can be withdrawn from the sleeve and uncoiled in readiness for use.

11. The oral wipe of claim 10 wherein the sleeve of interwoven material is saturated with a mouth wash.

12. The oral wipe of claim 10 wherein the sleeve has a partially open side remote from said corner to enable a finger to be readily inserted in said sleeve.

13. The oral wipe of claim 8 wherein the sleeve is comprised of a folded piece of said interwoven material, said heat seal means extending partially along longitudinal edges of an open side of the folded piece for coupling the edges of the sleeve to thereby provide a open ended sleeve.

14. The oral wipe of claim 8 wherein the sleeve pick element and floss are enclosed in a pouch for sanitary purposes in readiness for use.

15. The oral wipe of claim 14 wherein said pouch is comprised of a heat sealable aluminum material which totally seals the sleeve pick element and floss from outside environment.

16. The oral wipe of claim 15 wherein said pouch is heated to at least 250 degrees F. to imperically sterilize the oral wipe.

17. The oral wipe of claim 8 wherein the pick element is provided with a rounded terminal having a rounded point for reaching in to clean crevices between teeth and for cleaning gum tissue.

18. The oral wipe of claim 8 wherein the pick element has at least one pointed end for reaching in and cleaning crevices between teeth.

19. The oral wipe of claim 8 wherein the pick element has a V-shaped end for reaching in and cleaning crevices between teeth.

* * * * *